(12) United States Patent
Souza et al.

(10) Patent No.: US 10,632,107 B2
(45) Date of Patent: Apr. 28, 2020

(54) CRYSTALLINE FORMS OF BENZOQUINOLINE INHIBITORS OF VESICULAR MONOAMINE TRANSPORTER 2

(71) Applicant: Apotex Inc., Toronto (CA)

(72) Inventors: Fabio E. S. Souza, Mississauga (CA); Bahareh Khalili, Mississauga (CA); Allan W. Rey, Brantford (CA)

(73) Assignee: Apotex Inc., Toronto, Ontario (CA)

( * ) Notice: Subject to any disclaimer, the term of this patent is extended or adjusted under 35 U.S.C. 154(b) by 0 days.

(21) Appl. No.: 16/410,248

(22) Filed: May 13, 2019

(65) Prior Publication Data

US 2019/0343815 A1 Nov. 14, 2019

Related U.S. Application Data

(60) Provisional application No. 62/671,002, filed on May 14, 2018.

(51) Int. Cl.
| | | |
|---|---|---|
| A61K 31/4375 | (2006.01) | |
| A61K 31/353 | (2006.01) | |
| A61P 39/06 | (2006.01) | |
| A61P 25/28 | (2006.01) | |
| A61K 9/20 | (2006.01) | |

(52) U.S. Cl.
CPC ............ *A61K 31/4375* (2013.01); *A61K 9/20* (2013.01); *A61K 31/353* (2013.01); *A61P 25/28* (2018.01); *A61P 39/06* (2018.01); *C07B 2200/13* (2013.01)

(58) Field of Classification Search
CPC .................................................. A61K 31/4375
USPC .......................................................... 549/94
See application file for complete search history.

(56) References Cited

U.S. PATENT DOCUMENTS

| | | |
|---|---|---|
| 2,830,993 A | 4/1958 | Brossi et al. |
| 8,524,733 B2 | 9/2013 | Gant et al. |
| 9,233,959 B2 | 1/2016 | Sommer et al. |

FOREIGN PATENT DOCUMENTS

| | | |
|---|---|---|
| WO | 2010044981 A2 | 4/2010 |
| WO | 2011019956 A2 | 2/2011 |
| WO | 2012081031 A1 | 6/2012 |
| WO | 2014047167 A1 | 3/2014 |
| WO | 2015175505 A1 | 11/2015 |
| WO | 2017221169 A1 | 12/2017 |

OTHER PUBLICATIONS

Bernstein, "Polymorphism in Molecular Crystals", Oxford University Press, 2002, p. 9-10.
Porter, "Coating of Pharmaceutical Dosage Forms", Remington: The Science and Practice of Pharmacy, 21st Edition, New York: Lippincott Williams & Wilkins, 2005, pp. 929-938.
Rudnic, et al., "Oral Solid Dosage Forms", Remington: The Science and Practice of Pharmacy, 21st Edition, New York: Lippincott Williams & Wilkins, 2005 p. 889-928.
Teva Pharmaceuticals USA, Inc., "Highlights of Prescribing Information", Reference ID 4078379, 2017, p. 1-22.

*Primary Examiner* — Nizal S Chandrakumar
(74) *Attorney, Agent, or Firm* — The Webb Law Firm (57) ABSTRACT

The present invention provides crystalline forms of Deutetrabenazine. Specific crystalline forms provided by the present invention include Deutetrabenazine Form APO-I, a co-crystal of Deutetrabenazine and quercetin, and Deutetrabenazine Form APO-II, a co-crystal of Deutetrabenazine and luteolin. Also provided are pharmaceutical compositions including the Deutetrabenazine crystalline forms, and the use of these forms in the treatment of tardive dyskinesia and chorea associated with Huntington's disease.

16 Claims, 4 Drawing Sheets

CRYSTALLINE FORMS OF BENZOQUINOLINE INHIBITORS OF VESICULAR MONOAMINE TRANSPORTER 2

CROSS-REFERENCE TO RELATED APPLICATION

This application claims the benefit of U.S. Provisional Patent Application No. 62/671,002, filed May 14, 2018, the disclosure of which is hereby incorporated in its entirety by reference.

TECHNICAL FIELD

The present invention is directed to crystalline forms of benzoquinoline inhibitors of vesicular monoamine transporter 2 (VMAT2), pharmaceutical compositions containing these forms, and their use to treat tardive dyskinesia and/or chorea associated with Huntington's disease.

BACKGROUND

The racemic benzoquinoline compounds rel-(3R,11bR)-1,3,4,6,7,11b-hexahydro-9,10-dimethoxy-3-(2-methylpropyl)-2H-benzo[a]quinolizin-2-one (1), commonly known as Tetrabenazine, and a deuterated analogue thereof, rel-(3R,11bR)-1,3,4,6,7,11b-hexahydro-9,10-di(methoxy-$d_6$) (2), commonly known as Deutetrabenazine, are vesicular monoamine transporter 2 (VMAT2) inhibitors. Tetrabenazine, which was first prepared in the 1950s, as described in, for example, U.S. Pat. No. 2,830,993 A, is marketed in the United States as XENAZINE®, and is indicated for the treatment of chorea associated with Huntington's disease. Deutetrabenazine, which is described in WO 2010/044981 A1, is marketed in the United States as AUSTEDO®, is also indicated for the treatment of chorea associated with Huntington's disease, as well for the treatment of tardive dyskinesia in adults.

Crystalline forms of Tetrabenazine are reported in WO 2012/081031 A1 and WO 2015/175505 A1, and those of Deutetrabenazine are reported in WO 2014/047167 A1. WO 2017/221169 A1 further reports crystalline pre-mixes of Deutetrabenazine with magnesium stearate and talc.

WO 2015/175505 A1 reports that XENAZINE® tablets are provided as an immediate release formulation. Tetrabenazine exhibits a pH-dependent solubility, having slight solubility at the low pH of the stomach, but being practically insoluble at pH values of greater than 4, which are present further down the gastrointestinal tract. As such, the immediate release formulation is intended to provide complete dissolution in the stomach. However, rapid dissolution from this formulation has been reported to lead to high peak plasma concentrations, which are believed to be associated with the occurrence side effects.

Modified/sustained release formulations of Tetrabenazine are disclosed in WO 2011/019956 A1 and WO 2015/175505 A1, which aim to alter the pharmacokinetic profile of Tetrabenazine, or metabolites thereof, and overcome problems associated with the immediate release formulation. However, owing to the low solubility of the Tetrabenazine in the higher pH regions of the gastrointestinal tract where the majority of the dissolution is expected to occur from a modified/sustained release formulation, there are concerns that complete dissolution of the administered dose may not occur for these types of formulations.

WO 2014/047167 A1 reports extended release formulations of Deutetrabenazine, which, together with the deuterium isotope effect, are expected to benefit patients by altering the pharmacokinetic profile of the drug substance. However, as for the modified release formulations of Tetrabenazine, problems could arise with extended release formulations as a result of the poor solubility of the active substance in the higher pH regions of the gastrointestinal tract.

Approaches to improving the solubility of a drug substance include, for example, particle size reduction techniques, dispersion of the drug substance onto an inert carrier, and formulation of the drug substance together with solubilizing excipients. A further approach, which is used in the modified release formulations described in WO 2015/175505 A1, comprises the use of an amorphous solid dispersion. However, amorphous forms tend to have lower stability compared to crystalline forms, and methods for their preparation can be complex on an industrial scale.

Different crystalline forms of the same compound may have different crystal packing, thermodynamic, spectroscopic, kinetic, surface and mechanical properties. For example, different crystalline forms may have different stability properties such that a particular crystalline form may be less sensitive to heat, relative humidity (RH) and/or light. Alternatively or additionally, a particular crystalline form may provide more favourable compressibility and/or density properties, thereby providing more desirable characteristics for formulation and/or product manufacturing. Differences in stability between solid forms of a drug may result from changes in chemical reactivity, such as differential oxidation. Particular crystalline forms may also have different solubilities, thereby providing different pharmacokinetic parameters, which allow for specific crystalline forms to be used in order to achieve specific pharmacokinetic targets. Differences in solubility between crystalline forms are particularly relevant for compounds exhibiting pH-dependent solubility, such as Tetrabenazine and Deutetrabenazine, wherein an enhancement in the solubility at higher pH values can provide an opportunity to prepare modified-release formulations where dissolution is possible further into the higher pH regions of the gastrointestinal tract, thereby delivering a greater percentage of drug per dose.

Although general approaches to the preparation of crystalline forms of active pharmaceutical ingredients are known, it is well established that the prediction of whether any given compound will exhibit polymorphism is not possible. Accordingly, it is not possible to extend generalities to the number and kinds of crystalline forms that can exist for Tetrabenazine and Deutetrabenazine, or to the methods that will be suitable for the preparation of any given crystalline form. Furthermore, prediction of the properties of any unknown crystalline forms, and how they will differ from other crystalline forms of the same compound, remains elusive (Joel Bernstein, *Polymorphism in Molecular Crystals*, Oxford University Press, New York, 2002, page 9).

In addition to the use of different crystalline forms to modify the physicochemical properties of a drug, it is also known that the physicochemical properties of a drug can be modified through the formation of co-crystals, wherein a drug molecule and a co-former co-crystallize within the same crystal lattice. However, methods are not available to predict the compounds that can successfully serve as co-formers with a particular drug or the conditions required to successfully co-crystallize two compounds within the same crystal lattice.

In view of the problems associated with the existing formulations of Tetrabenazine and Deutetrabenazine, there exists a need for novel crystalline forms of these compounds for use in the preparation of drug products providing improved properties, and methods for their manufacture.

SUMMARY

The crystalline forms of the present invention comprise one of Tetrabenazine or Deutetrabenazine co-crystallized with an equimolar amount of one of luteolin or quercetin. Luteolin and quercetin are anti-oxidants naturally occurring in foods. As such, it is expected that they can safely be used in materials intended for use in the preparation of pharmaceutical compositions intended for administration to humans or animals. Since the commercial AUSTEDO® tablets contain the anti-oxidative agents butylated hydroxytoluene (BHT) and butylated hydroxyanisole (BHA), presumably to protect against oxidation in the drug product, it is expected that, in addition to serving as co-formers to provide novel crystalline forms of Tetrabenazine or Deutetrabenazine, the anti-oxidant properties of quercetin and luteolin may serve as substitutes for BHT and/or BHA in drug products.

The present invention provides crystalline forms of Tetrabenazine and Deutetrabenazine that can be prepared by efficient and industrially compatible processes using Class 3 solvents established by the ICH (International Council for Harmonisation of Technical Requirements for Pharmaceuticals for Human Use) as having low toxicity. Additionally, the crystalline forms of the present invention exhibit stability when exposed to conditions of high temperature and high humidity.

Accordingly, in a first aspect of the present invention, there is provided a crystalline form of Deutetrabenazine comprising Deutetrabenazine and quercetin. Preferably, in the crystalline form of the first aspect, the molar ratio of Deutetrabenazine to quercetin is between approximately 1:0.75 and 1:1.25. Most preferably, the molar ratio of Deutetrabenazine to quercetin is approximately 1:1.

In a second aspect of the present invention, there is provided a crystalline form of Deutetrabenazine, APO-I, comprising Deutetrabenazine and quercetin, characterized by a PXRD diffractogram comprising peaks, expressed in degrees 2θ (±0.2°), at 6.2°, 9.3° and 14.1°. In a preferred embodiment of the second aspect, the PXRD diffractogram further comprises at least three peaks, expressed in degrees 2θ (±0.2°), selected from the group consisting of: 6.9°, 10.3°, 11.1°, 12.4°, 15.7° and 18.6°. In a further preferred embodiment of the second aspect, the PXRD diffractogram further comprises peaks, expressed in degrees 2θ (±0.2°), at 6.9°, 10.3°, 11.1°, 12.4°, 15.7° and 18.6°. Preferably, the crystalline form of the second aspect of the invention provides a PXRD diffractogram comprising peaks in substantially the same positions (±0.2° 2θ) as those shown in FIG. 1. In a further preferred embodiment of the second aspect, the molar ratio of Deutetrabenazine to quercetin is approximately 1:1.

In a third aspect of the present invention, there is provided a crystalline form of Deutetrabenazine comprising Deutetrabenazine and luteolin. Preferably, in the crystalline form of the third aspect, the molar ratio of Deutetrabenazine to luteolin is between approximately 1:0.75 and 1:1.25. Most preferably, the molar ratio of Deutetrabenazine to luteolin is approximately 1:1.

In a fourth aspect of the present invention, there is provided a crystalline form of Deutetrabenazine, APO-II, comprising Deutetrabenazine and luteolin, characterized by a PXRD diffractogram comprising peaks, expressed in degrees 2θ (±0.2°), at 6.2°, 9.3° and 14.2°. In a preferred embodiment of the fourth aspect, the PXRD diffractogram further comprises at least three peaks, expressed in degrees 2θ (±0.2°), selected from the group consisting of: 6.9°, 10.3°, 11.1°, 12.4°, 15.7° and 18.6°. In a further preferred embodiment of the fourth aspect, the PXRD diffractogram further comprises peaks, expressed in degrees 2θ (±0.2°), 6.9°, 10.3°, 11.1°, 12.4°, 15.7° and 18.6°. Preferably, the crystalline form of the fourth aspect of the invention provides a PXRD diffractogram comprising peaks in substantially the same positions (±0.2° 2θ) as those shown in FIG. 2. In a further preferred embodiment of the fourth aspect, the molar ratio of Deutetrabenazine to luteolin is approximately 1:1.

In a fifth aspect of the present invention, there is provided a crystalline form of Tetrabenazine comprising Tetrabenazine and quercetin. Preferably, in the crystalline form of the fifth aspect, the molar ratio of Tetrabenazine to quercetin is between approximately 1:0.75 and 1:1.25. Most preferably, the molar ratio of Tetrabenazine to quercetin is approximately 1:1.

In a sixth aspect of the present invention, there is provided a crystalline form of Tetrabenazine, APO-I, comprising Tetrabenazine and quercetin, characterized by a PXRD diffractogram comprising peaks, expressed in degrees 2θ (±0.2°), at 6.3°, 9.4° and 14.3°. In a preferred embodiment of the sixth aspect, the PXRD diffractogram further comprises at least three peaks, expressed in degrees 2θ (±0.2°), selected from the group consisting of: 6.9°, 7.0°, 10.4°, 11.1°, 12.5°, 15.8° and 18.8°. In a further preferred embodiment of the sixth aspect, the PXRD diffractogram further comprises peaks, expressed in degrees 2θ (±0.2°), at 7.0°, 10.4°, 11.1°, 12.5°, 15.8° and 18.8°. Preferably, the crystalline form of the sixth aspect of the invention provides a PXRD diffractogram comprising peaks in substantially the same positions (±0.2° 2θ) as those shown in FIG. 3. In a further preferred embodiment of the sixth aspect, the molar ratio of Tetrabenazine to quercetin is approximately 1:1.

In a seventh aspect of the present invention, there is provided a crystalline form of Tetrabenazine comprising Tetrabenazine and luteolin. Preferably, in the crystalline form of the seventh aspect, the molar ratio of Tetrabenazine to luteolin is between approximately 1:0.75 and 1:1.25. Most preferably, the molar ratio of Tetrabenazine to luteolin is approximately 1:1.

In an eighth aspect of the present invention, there is provided a crystalline form of Tetrabenazine, APO-II, comprising Tetrabenazine and luteolin, characterized by a PXRD diffractogram comprising peaks, expressed in degrees 2θ (±0.2°), at 6.3°, 9.4° and 14.4°. In a preferred embodiment of the eighth aspect, the PXRD diffractogram further comprises at least three peaks, expressed in degrees 2θ (±0.2°), selected from the group consisting of: 7.0°, 10.6°, 11.3°, 12.6°, 16.1° and 18.9°. In a further preferred embodiment of the eighth aspect, the PXRD diffractogram further comprises peaks, expressed in degrees 2θ (±0.2°), 7.0°, 10.6°, 11.3°, 12.6°, 16.1° and 18.9°. Preferably, the crystalline form of the eighth aspect of the invention provides a PXRD diffractogram comprising peaks in substantially the same positions (±0.2° 2θ) as those shown in FIG. 4. In a further preferred embodiment of the eighth aspect, the molar ratio of Tetrabenazine to luteolin is approximately 1:1.

In a ninth aspect of the present invention, there is provided a pharmaceutical composition comprising a crystalline form of Deutetrabenazine according to any one of the first, second, third or fourth aspects of the invention, and one or more pharmaceutically acceptable excipients. Preferably, the pharmaceutical composition is in the form of a solid dosage form. Most preferably, the pharmaceutical composition is a tablet.

In a tenth aspect of the present invention, there is provided a use of a crystalline form of Deutetrabenazine according to any one of the first, second, third or fourth aspects of the invention, or the pharmaceutical composition of the ninth aspect of the invention, in the treatment of tardive dyskinesia or chorea associated with Huntington's disease.

In an eleventh aspect of the present invention, there is provided a pharmaceutical composition comprising a crystalline form of Tetrabenazine according to any one of the fifth, sixth, seventh or eighth aspects of the invention, and one or more pharmaceutically acceptable excipients. Preferably, the pharmaceutical composition is in the form of a solid dosage form. Most preferably, the pharmaceutical composition is a tablet.

In a twelfth aspect of the present invention, there is provided a use of a crystalline form of Tetrabenazine according to any one of the fifth, sixth, seventh or eighth aspects of the invention, or the pharmaceutical composition of the eleventh aspect of the invention, in the treatment of tardive dyskinesia or chorea associated with Huntington's disease.

In a thirteenth aspect of the present invention, there is provided a pharmaceutical composition comprising a mixture of two or more crystalline forms of Deutetrabenazine and Tetrabenazine according to any one of the first through eighth aspects of the invention, and one or more pharmaceutically acceptable excipients. Preferably, the pharmaceutical composition is in the form of a solid dosage form. Most preferably, the pharmaceutical composition is a tablet.

In a fourteenth aspect of the present invention, there is provided a use of a mixture of two or more of the crystalline form of Deutetrabenazine and Tetrabenazine according to any one of the first through eighth aspects of the invention, or the pharmaceutical composition of the thirteenth aspect of the invention, in the treatment of tardive dyskinesia or chorea associated with Huntington's disease.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention are described, by way of example only, with reference to the attached Figures.

DETAILED DESCRIPTION

The benzoquinoline crystalline forms of the present invention comprise one of Tetrabenazine or Deutetrabenazine crystallized together with one of luteolin or quercetin within the same crystal lattice. Importantly, with respect to the use of the crystalline forms of the present invention in the preparation of pharmaceutical compositions for use in the treatment of chronic illnesses such as Huntington's disease, luteolin and quercetin are non-toxic flavonoid compounds having anti-oxidant properties that are commonly found at relatively high levels in fruits and vegetables, and are also sold as health supplements. Thus, in addition to serving as co-formers in the formation of the crystalline forms of the present invention to modify the physicochemical properties of Tetrabenazine and Deutetrabenazine, the presence of luteolin and quercetin within the crystalline forms provides a natural anti-oxidant, which will benefit both the patient and provide a stabilizing effect to the active ingredients. For example, commercial forms of Deutetrabenazine contain two different anti-oxidants, BHT and BHA, presumably to protect the active ingredient from oxidation.

The Tetrabenazine and Deutetrabenazine crystalline forms of the present invention exhibit differences in properties when compared to the known crystalline forms of these compounds. Properties that differ between the invention and known crystalline forms of Tetrabenazine and Deutetrabenazine include crystal packing properties such as molar volume, density and hygroscopicity; thermodynamic properties such as melting point and solubility; kinetic properties such as dissolution rate and chemical/polymorphic stability; surface properties such as crystal habit/particle morphology; and/or mechanical properties such as hardness, tensile strength, compactibility, tableting, handling, flow, and blending.

Furthermore, the present invention provides crystalline forms of Tetrabenazine and Deutetrabenazine that can be prepared by efficient and industrially compatible processes using Class 3 alcohol solvents established by the ICH as having low toxicity. Additionally, the crystalline forms of the present invention exhibit stability when exposed to conditions of 40° C./75% RH.

Depending on the manner in which the embodiments of the invention are prepared, the methodology and instrument used for PXRD analysis, the intensity of a given peak observed in a PXRD diffractogram of a crystalline form may vary when compared to the same peak in the representative PXRD diffractograms provided in FIGS. 1 to 4. Thus, differences in relative peak intensities between peaks in a PXRD diffractogram for a given crystalline form may be observed when compared to the relative peak intensities of the peaks in the representative PXRD diffractograms of FIGS. 1 to 4. Any such differences may be due, in part, to the preferred orientation of the sample and its deviation from the ideal random sample orientation, the preparation of the sample for analysis, and the methodology applied for the analysis. Such variations are known and understood by a person of skill in the art, and any such variations do not depart from the invention disclosed herein.

In addition to the differences in relative peak intensities that may be observed in comparison to the representative PXRD diffractograms provided in FIGS. 1 to 4, it is understood that individual peak positions may vary between ±0.2° 2θ from the values observed in the representative PXRD diffractograms provided in FIGS. 1 to 4 for the crystalline forms of the invention, or listed in Tables 1 to 4. Such variations are known and understood by a person of skill in the art, and any such variations do not depart from the invention disclosed herein.

Further, depending on the instrument used for X-ray analysis and its calibration, uniform offsets in the peak position of each peak in a PXRD diffractogram of greater that 0.2° 2θ may be observed when compared to the representative PXRD diffractograms provided in FIGS. 1 to 4. Thus, PXRD diffractograms of the crystalline forms of the present invention may, in some circumstances, display the same relative peak positions as observed in the representative PXRD diffractograms provided in FIGS. 1 to 4, with the exception that each peak is offset in the same direction, and by approximately the same amount, such that the overall PXRD diffractogram is substantially the same in appearance as a PXRD diffractogram of FIGS. 1 to 4, with the exception of the uniform offset in peak positions. The observation of any such uniform peak shift in a PXRD diffractogram does not depart from the invention disclosed herein given that the relative peak positions of the individual peaks within the PXRD diffractogram remain consistent with the relative peak positions observed in the PXRD diffractograms of FIGS. 1 to 4.

As used herein, the term 'crystalline form' refers to a substance with a particular arrangement of molecular components in its crystal lattice, and which may be identified by physical characterization methods such as PXRD. As used herein, the term crystalline form is intended to include single-component and multiple-component crystalline forms of Tetrabenazine and to include single-component and multiple-component crystalline forms of Deutetrabenazine. Single-component forms of Tetrabenazine consist solely of Tetrabenazine in the repeating unit of the crystal lattice and single-component forms of Deutetrabenazine consist solely of Deutetrabenazine in the repeating unit of the crystal lattice. Multiple-component forms of Tetrabenazine such as the crystalline forms of the present invention include crystalline forms of Tetrabenazine wherein one or more other co-former molecules are also incorporated into the crystal lattice with Tetrabenazine, and multiple-component forms of Deutetrabenazine, such as the crystalline forms of the present invention, include crystalline forms of Deutetrabenazine wherein one or more other co-former molecules are also incorporated into the crystal lattice with Deutetrabenazine.

As used herein, the term 'co-crystal' refers to a multiple-component crystalline form containing both Tetrabenazine and a co-former, and to a multiple-component crystal form of Deutetrabenazine and a co-former, wherein the co-formers are solid under ambient conditions.

Multi-component crystalline forms comprising more than one type of molecule, such as co-crystals, may have some variability in the exact molar ratio of their components depending on a variety of conditions used. For example, a molar ratio of components within a multi-component crystalline form provides a person of skill in the art information as to the general relative quantities of the components of the crystalline form. In many cases, the molar ratio may vary by ±20% from a stated range. For example, with respect to the present invention, a molar ratio of 1:1 should be understood to include the ratios 1:0.8 and 1:1.2, as well as all of the individual ratios in between.

As used herein, the term "room temperature" refers to a temperature in the range of 20° C. to 25° C.

Unless defined otherwise herein, the term "approximately", when used in reference to molar ratios, allows for a variance of plus or minus 10%.

When describing the embodiments of the present invention there may be a common variance to a given temperature or time that would be understood or expected by the person skilled in the art to provide substantially the same result. For example, when reference is made to a particular temperature, it is to be understood by the person skilled in the art that there is an allowable variance of ±5° C. associated with that temperature. When reference is made to a particular time, it is to be understood that there is an allowable variance of ±10 minutes when the time is one or two hours, and ±1 hour when longer periods of time are referenced.

In one embodiment of the present invention, there is provided a new crystalline form of Deutetrabenazine, Deutetrabenazine Form APO-I, which is a co-crystal of Deutetrabenazine and quercetin. Preferably, in Deutetrabenazine APO-I, the molar ratio of Deutetrabenazine to quercetin is approximately 1:1.

Deutetrabenazine Form APO-I can be characterized by a PXRD diffractogram comprising, among other peaks, characteristic peaks, expressed in degrees 2θ (±0.2°), at 6.2°, 9.3° and 14.1°. Preferably, the PXRD diffractogram further comprises at least three peaks, expressed in degrees 2θ (±0.2°), selected from the group consisting of 6.9°, 10.3°, 11.1°, 12.4°, 15.7° and 18.6°. More preferably, the PXRD diffractogram further comprises peaks, expressed in degrees 2θ (±0.2°), at 6.9°, 10.3°, 11.1°, 12.4°, 15.7° and 18.6°. PXRD studies of capped and uncapped samples of Deutetrabenazine Form APO-I have shown that this crystal form is stable following storage in stability chambers maintained at 27° C./60% RH and 40° C./75% RH for at least one month.

Figure 1:
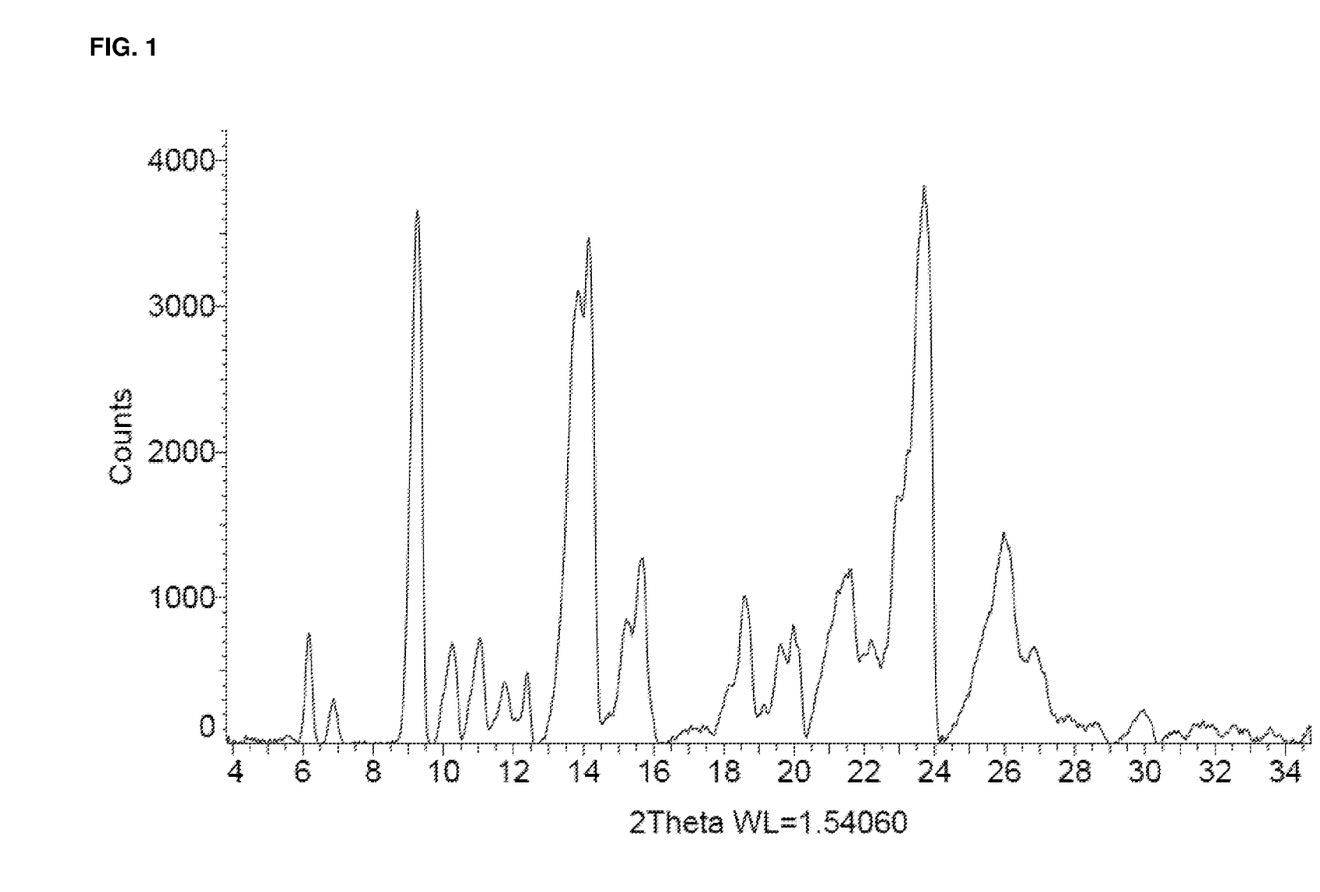
FIG. 1 is a representative PXRD diffractogram of Deutetrabenazine Form APO-I as prepared in Example 1.

An illustrative PXRD diffractogram of Deutetrabenazine Form APO-I, as prepared in Example 1, is shown in FIG. 1. A peak listing, comprising representative peaks from the PXRD diffractogram in FIG. 1, and their relative intensities, is provided in Table 1. Although illustrative of the PXRD diffractogram that is provided for the Deutetrabenazine Form APO-I of the present invention, the relative intensities of the peaks are variable. Thus, depending on a particular sample, the prominence or relative intensity of the peaks observed may differ from those in the illustrative PXRD diffractogram and peak listing.

TABLE 1

Relative peak intensities of Deutetrabenazine Form APO-I from FIG. 1

| Angle (° 2θ) | Relative intensity (%) |
|---|---|
| 6.18 | 19.7 |
| 6.88 | 8.1 |
| 9.26 | 95.6 |
| 10.26 | 18.1 |
| 11.05 | 18.8 |
| 11.76 | 11.0 |
| 12.40 | 12.7 |
| 13.89 | 80.4 |
| 14.14 | 90.7 |
| 15.25 | 21.7 |
| 15.67 | 33.2 |
| 18.59 | 26.5 |

TABLE 1-continued

Relative peak intensities of
Deutetrabenazine Form APO-I from FIG. 1

| Angle (° 2θ) | Relative intensity (%) |
|---|---|
| 19.61 | 17.8 |
| 19.98 | 21.2 |
| 21.47 | 30.3 |
| 23.71 | 100.00 |
| 25.98 | 37.7 |

Deutetrabenazine Form APO-I can be prepared by combining quercetin, preferably quercetin dihydrate, with Deutetrabenazine in a solvent, preferably 2-methyl-1-propanol, at a suitable temperature, preferably in the range of 40° C. to 60° C., followed by a period of cooling. Alternatively, acetone or isopropyl acetate can be used as the solvent. The molar ratio of Deutetrabenazine to quercetin is at least approximately 1:1. Filtration of the resulting suspension and drying, if necessary, provides Deutetrabenazine Form APO-I having a PXRD diffractogram consistent with FIG. 1.

In a second embodiment of the present invention, there is provided a new crystalline form of Deutetrabenazine, Deutetrabenazine Form APO-II, which is a co-crystal of Deutetrabenazine and luteolin. Preferably, in Deutetrabenazine Form APO-II, the molar ratio of Deutetrabenazine to luteolin is approximately 1:1.

Deutetrabenazine Form APO-II can be characterized by a PXRD diffractogram comprising, among other peaks, characteristic peaks, expressed in degrees 2θ (±0.2°), at 6.2°, 9.3° and 14.2°. Preferably, the PXRD diffractogram further comprises at least three peaks, expressed in degrees 2θ (±0.2°), selected from the group consisting of 6.9°, 10.5°, 11.1°, 12.4°, 16.0° and 18.7°. More preferably, the PXRD diffractogram further comprises peaks, expressed in degrees 2θ (±0.2°), at 6.9°, 10.5°, 11.1°, 12.4°, 16.0° and 18.7°. PXRD studies of capped and uncapped samples of Deutetrabenazine Form APO-II have shown that this crystal form is stable following storage in stability chambers maintained at 27° C./60% RH and 40° C./75% RH for at least one month.

Figure 2:
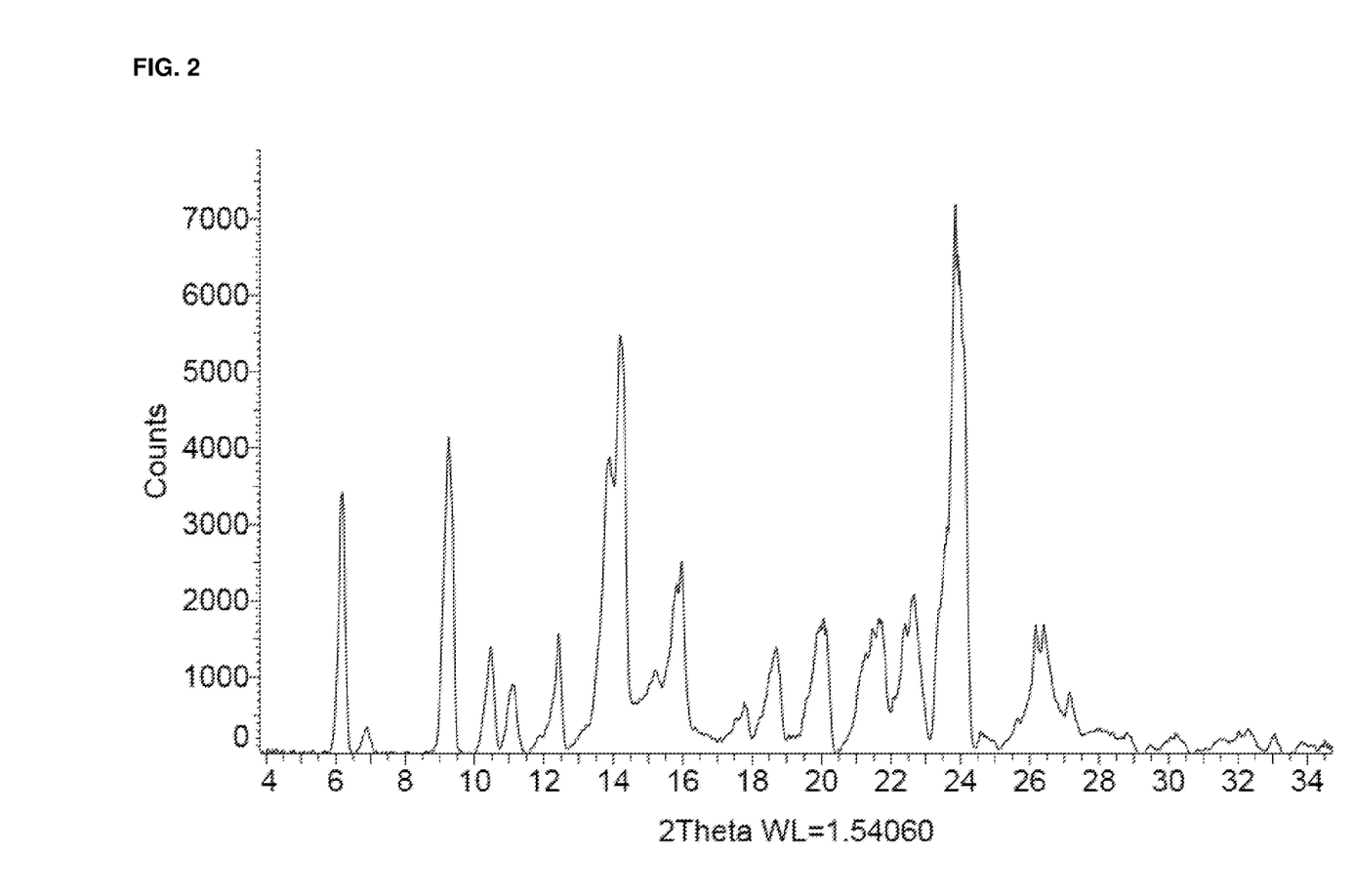
FIG. 2 is a representative PXRD diffractogram of Deutetrabenazine Form APO-II as prepared in Example 2.

An illustrative PXRD diffractogram of Deutetrabenazine Form APO-II, as prepared in Example 2, is shown in FIG. 2. A peak listing, comprising representative peaks from the PXRD diffractogram in FIG. 2, and their relative intensities, is provided in Table 2. Although illustrative of the PXRD diffractogram that is provided for the Deutetrabenazine Form APO-II of the present invention, the relative intensities of the peaks are variable. Thus, depending on a particular sample, the prominence or relative intensity of the peaks observed may differ from those in the illustrative PXRD diffractogram and peak listing.

TABLE 2

Relative peak intensities of
Deutetrabenazine Form APO-II from FIG. 2

| Angle (° 2θ) | Relative intensity (%) |
|---|---|
| 6.19 | 52.2 |
| 6.90 | 5.2 |
| 9.26 | 63.3 |
| 10.47 | 21.3 |
| 11.11 | 13.7 |
| 12.43 | 23.9 |
| 13.90 | 59.3 |
| 14.20 | 83.8 |

TABLE 2-continued

Relative peak intensities of
Deutetrabenazine Form APO-II from FIG. 2

| Angle (° 2θ) | Relative intensity (%) |
|---|---|
| 15.22 | 16.7 |
| 15.97 | 38.3 |
| 18.70 | 21.2 |
| 20.05 | 27.0 |
| 21.67 | 26.9 |
| 22.66 | 31.8 |
| 23.92 | 100.00 |
| 26.41 | 25.7 |

Deutetrabenazine Form APO-II can be prepared by combining luteolin and Deutetrabenazine in a solvent, preferably a mixture of isopropyl alcohol and water, at a suitable temperature, preferably in the range of 40° C. to 60° C., followed by a period of cooling. Alternatively, mixtures of tetrahydrofuran and water can be used as the solvent. The molar ratio of Deutetrabenazine to luteolin is at least approximately 1:1. Filtration of the resulting suspension and drying, if necessary, provides Deutetrabenazine Form APO-II having a PXRD diffractogram consistent with FIG. 2.

In a third embodiment of the present invention, there is provided a new crystalline form of Tetrabenazine, Tetrabenazine Form APO-I, which is a co-crystal of Tetrabenazine and quercetin. Preferably, in Tetrabenazine Form APO-I, the molar ratio of Tetrabenazine to quercetin is approximately 1:1.

Tetrabenazine Form APO-I can be characterized by a PXRD diffractogram comprising, among other peaks, characteristic peaks, expressed in degrees 2θ (±0.2°), at 6.3°, 9.4° and 14.3°. Preferably, the PXRD diffractogram further comprises at least three peaks, expressed in degrees 2θ (±0.2°), selected from the group consisting of 7.0°, 10.4°, 11.1°, 12.5°, 15.8° and 18.8°. More preferably, the PXRD diffractogram further comprises peaks, expressed in degrees 2θ (±0.2°), at 7.0°, 10.4°, 11.1°, 12.5°, 15.8° and 18.8°. PXRD studies of capped and uncapped samples of Tetrabenazine Form APO-I have shown that this crystal form is stable following storage in stability chambers maintained at 27° C./60% RH and 40° C./75% RH for at least one month.

Figure 3:
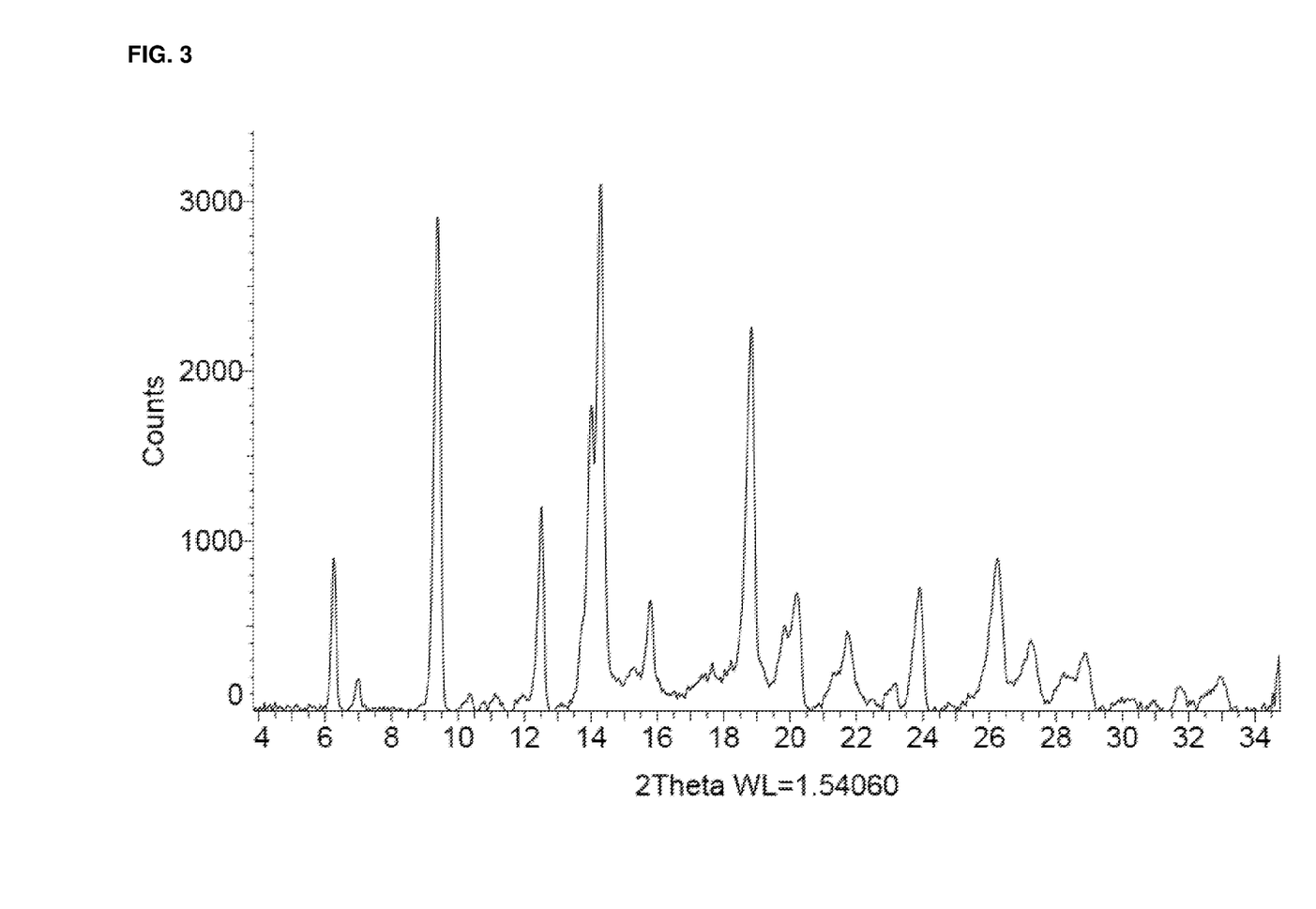
FIG. 3 is a representative PXRD diffractogram of Tetrabenazine Form APO-I as prepared in Example 3.

An illustrative PXRD diffractogram of Tetrabenazine Form APO-I, as prepared in Example 3, is shown in FIG. 3. A peak listing, comprising representative peaks from the PXRD diffractogram in FIG. 3, and their relative intensities, is provided in Table 3. Although illustrative of the PXRD diffractogram that is provided for the Tetrabenazine Form APO-I of the present invention, the relative intensities of the peaks are variable. Thus, depending on a particular sample, the prominence or relative intensity of the peaks observed may differ from those in the illustrative PXRD diffractogram and peak listing.

TABLE 3

Relative peak intensities of
Tetrabenazine Form APO-I from FIG. 3

| Angle (° 2θ) | Relative intensity (%) |
|---|---|
| 6.26 | 28.9 |
| 7.00 | 6.0 |
| 9.39 | 93.9 |
| 10.37 | 3.2 |
| 11.12 | 3.2 |
| 12.51 | 38.8 |

TABLE 3-continued

Relative peak intensities of
Tetrabenazine Form APO-I from FIG. 3

| Angle (° 2θ) | Relative intensity (%) |
|---|---|
| 14.02 | 57.9 |
| 14.30 | 100.0 |
| 15.80 | 21.0 |
| 18.84 | 72.9 |
| 19.83 | 16.2 |
| 20.20 | 22.4 |
| 21.73 | 15.1 |
| 23.90 | 23.5 |
| 26.25 | 29.0 |

Tetrabenazine Form APO-I can be prepared by combining quercetin, preferably quercetin dihydrate, with Tetrabenazine in a solvent, preferably 2-methyl-1-propanol at a suitable temperature, preferably in the range of 40° C. to 60° C., followed by a period of cooling. Alternatively, acetone or isopropyl acetate can be used as the solvent. The molar ratio of Tetrabenazine to quercetin is at least approximately 1:1. Filtration of the resulting suspension and drying, if necessary, provides Tetrabenazine Form APO-I having a PXRD diffractogram consistent with FIG. 3.

In a fourth embodiment of the present invention, there is provided a new crystalline form of Tetrabenazine, Tetrabenazine Form APO-II, which is a co-crystal of Tetrabenazine and luteolin. Preferably, in Tetrabenazine Form APO-II, the molar ratio of Tetrabenazine to luteolin is approximately 1:1.

Tetrabenazine Form APO-II can be characterized by a PXRD diffractogram comprising, among other peaks, characteristic peaks, expressed in degrees 2θ (±0.2°), at 6.3°, 9.4° and 14.4°. Preferably, the PXRD diffractogram further comprises at least three peaks, expressed in degrees 2θ (±0.2°), selected from the group consisting of 7.0°, 10.6°, 11.3°, 12.6°, 16.1° and 18.9°. More preferably, the PXRD diffractogram further comprises peaks, expressed in degrees 2θ (±0.2°), at 7.0°, 10.6°, 11.3°, 12.6°, 16.1° and 18.9°. PXRD studies of capped and uncapped samples of Tetrabenazine Form APO-II have shown that this crystal form is stable following storage in stability chambers maintained at 27° C./60% RH and 40° C./75% RH for at least one month.

Figure 4:
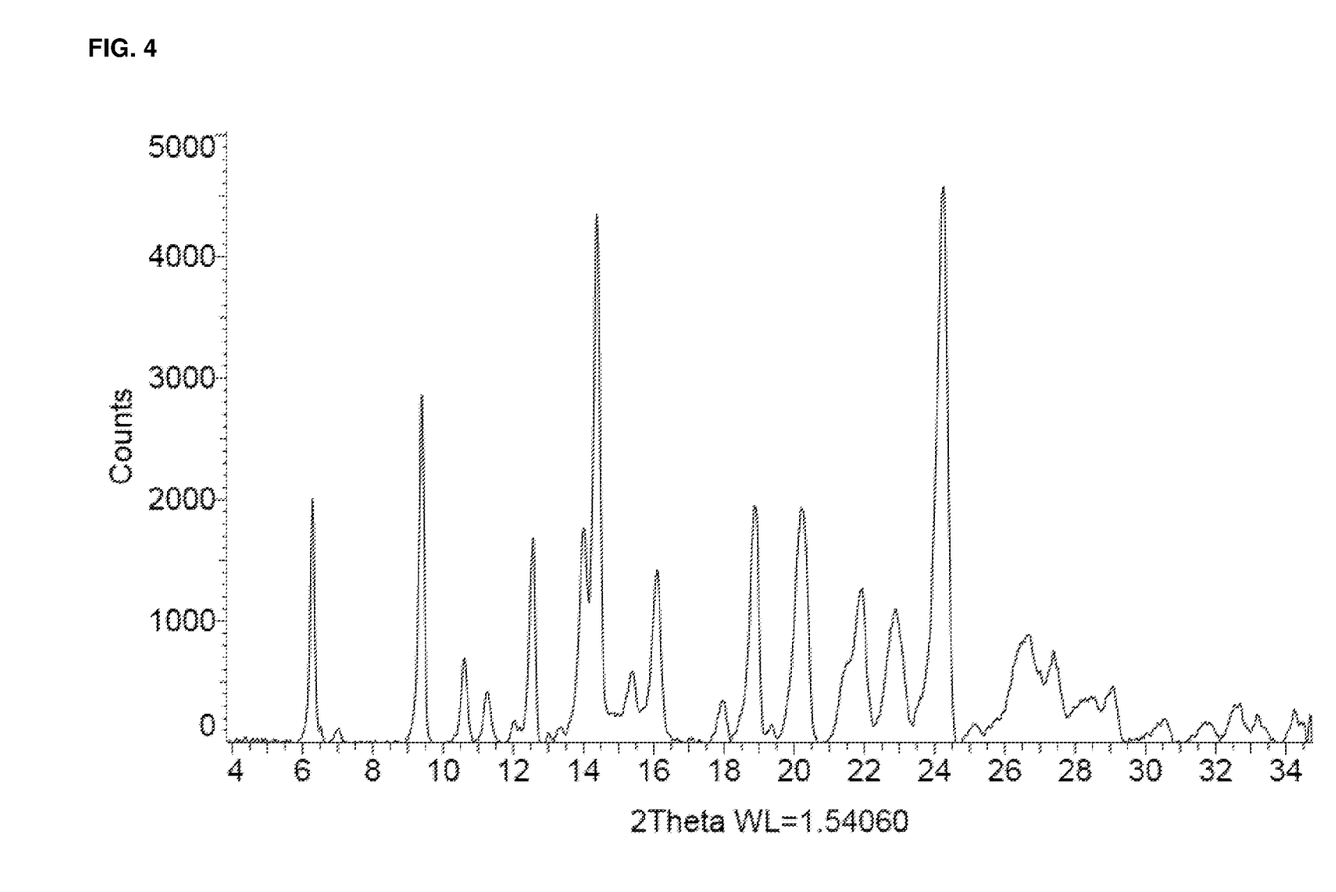
FIG. 4 is a representative PXRD diffractogram of Tetrabenazine Form APO-II as prepared in Example 4.

An illustrative PXRD diffractogram of Tetrabenazine Form APO-II, as prepared in Example 4, is shown in FIG. 4. A peak listing, comprising peaks from the PXRD diffractogram in FIG. 4, and their relative intensities, is provided in Table 4. Although illustrative of the PXRD diffractogram that is provided for the Tetrabenazine Form APO-II of the present invention, the relative intensities of the peaks are variable. Thus, depending on a particular sample, the prominence or relative intensity of the peaks observed may differ from those in the illustrative PXRD diffractogram and peak listing.

TABLE 4

Relative peak intensities of
Tetrabenazine Form APO-II from FIG. 4

| Angle (° 2θ) | Relative intensity (%) |
|---|---|
| 6.29 | 43.3 |
| 7.02 | 2.6 |
| 9.40 | 62.2 |
| 10.61 | 15.1 |
| 11.26 | 9.2 |

TABLE 4-continued

Relative peak intensities of
Tetrabenazine Form APO-II from FIG. 4

| Angle (° 2θ) | Relative intensity (%) |
|---|---|
| 12.56 | 36.7 |
| 14.00 | 38.5 |
| 14.38 | 94.7 |
| 15.39 | 12.8 |
| 16.10 | 30.9 |
| 18.88 | 42.5 |
| 20.21 | 42.3 |
| 21.93 | 27.6 |
| 22.89 | 23.9 |
| 24.25 | 100.0 |
| 26.65 | 19.5 |

Tetrabenazine Form APO-II can be prepared by combining luteolin and Tetrabenazine in a solvent, preferably a mixture of isopropyl alcohol and water, at a suitable temperature, preferably in the range of 40° C. to 60° C., followed by a period of cooling. Alternatively, mixtures of tetrahydrofuran and water can be used as the solvent. The molar ratio of Tetrabenazine to luteolin is at least approximately 1:1. Filtration of the resulting suspension and drying, if necessary, provides Tetrabenazine Form APO-II having a PXRD diffractogram consistent with FIG. 4.

In a further embodiment of the invention, there is provided a pharmaceutical composition of a crystalline form of Deutetrabenazine comprising co-crystallized Deutetrabenazine and quercetin or co-crystallized Deutetrabenazine and luteolin, with one or more pharmaceutically acceptable excipients. Preferably, the pharmaceutical composition is a solid dosage form suitable for oral administration, such as a capsule, tablet, pill, powder or granulate. Most preferably, the pharmaceutical composition is a tablet. Preferably, the pharmaceutical composition provides a dose of Deutetrabenazine that is equivalent to the 6 mg, 9 mg or 12 mg of Deutetrabenazine found in AUSTEDO® drug products.

In a further embodiment of the invention, there is provided a pharmaceutical composition of a crystalline form of Tetrabenazine comprising co-crystallized Tetrabenazine and quercetin or co-crystallized Tetrabenazine and luteolin, with one or more pharmaceutically acceptable excipients. Preferably, the pharmaceutical composition is a solid dosage form suitable for oral administration, such as a capsule, tablet, pill, powder or granulate. Most preferably, the pharmaceutical composition is a tablet. Preferably, the pharmaceutical composition provides a dose of Tetrabenazine that is equivalent to the 12.5 mg or 25 mg of Tetrabenazine found in XENAZINE® drug products.

In a further embodiment of the invention, there is provided a pharmaceutical composition comprising a mixture of two or more crystalline forms of Tetrabenazine or Deutetrabenazine co-crystallized with quercetin or luteolin as described here, with one or more pharmaceutically acceptable excipients. Preferably, the pharmaceutical composition is a solid dosage form suitable for oral administration, such as a capsule, tablet, pill, powder or granulate. Most preferably, the pharmaceutical composition is a tablet. Through the use of a combination of two or more of the crystalline forms of the present invention, the dissolution rate of the compositions can be tailored to provide a desired pharmacokinetic profile following administration.

Suitable pharmaceutically acceptable excipients are preferably inert with respect to the crystalline forms of Deutetrabenazine and Tetrabenazine of the present invention, and may include, for example, one or more excipients selected from binders such as lactose, starches, modified starches, sugars, gum acacia, gum tragacanth, guar gum, pectin, wax binders, microcrystalline cellulose, methylcellulose, carboxymethylcellulose, hydroxypropyl methylcellulose, hydroxyethyl cellulose, hydroxypropyl cellulose, copolyvidone, gelatine, polyvinylpyrollidone (PVP) and sodium alginate; fillers or diluents such as lactose, sugar, starches, modified starches, mannitol, sorbitol, inorganic salts, cellulose derivatives (e.g., microcrystalline cellulose, cellulose), calcium sulphate, xylitol and lactitol; disintegrants such as croscarmellose sodium, crospovidone, polyvinylpyrrolidone, sodium starch glycollate, corn starch, microcrystalline cellulose, hydroxypropyl methylcellulose and hydroxypropyl cellulose; lubricants such as magnesium stearate, magnesium lauryl stearate, sodium stearyl fumarate, stearic acid, calcium stearate, zinc stearate, potassium benzoate, sodium benzoate, myristic acid, palmitic acid, mineral oil, hydrogenated castor oil, medium-chain triglycerides, poloxamer, polyethylene glycol and talc; and dispersants or solubility enhancing agents, such cyclodextrins, glyceryl monostearate, hypromellose, meglumine, Poloxamer, polyoxyethylene castor oil derivatives, polyoxyethylene stearates, polyoxylglycerides, povidone, and stearic acid. Other excipients including preservatives, stabilisers, anti-oxidants, silica flow conditioners, antiadherents or glidants may be added as required. Other suitable excipients and the preparation of solid oral dosage forms is well known to person of skill in the art, and is described generally, for example, in *Remington The Science and Practice of Pharmacy 21$^{st}$ Edition* (Lippincott Williams & Wilkins: Philadelphia; 2006; Chapter 45).

Optionally, when the pharmaceutical compositions are solid dosage forms, the solid dosage forms may be prepared with coatings, such as enteric coatings and extended release coatings, using standard pharmaceutical coatings. Such coatings, and their application, are well known to persons skilled in the art, and are described, for example, in *Remington The Science and Practice of Pharmacy 21$^{st}$ Edition* (Lippincott Williams & Wilkins: Philadelphia; 2006; Chapter 47).

EXAMPLES

The following non-limiting examples are illustrative of some of the aspects and embodiments of the invention described herein.

The Tetrabenazine used as a starting material in the following examples was consistent with Form A, which is reported in WO 2012/081031 A1, whereas the Deutetrabenazine used as a starting material was consistent with Form I, which is reported in WO 2014/047167 A1. Other polymorphic forms are equally suitable as starting material, provided complete dissolution of the form occurs when preparing the novel crystalline forms of Tetrabenazine and Deutetrabenazine of the present invention.

PXRD Analysis:

PXRD diffractograms were recorded on a Bruker D8 Discover powder X-ray diffractometer (Bruker-AXS, Karlsruhe, Germany). The sample holder was oscillated along X and Y axes during some of the measurements. The generator was a Micro-focus X-ray source (IMSTube: Cu tube with 1.54184 A) with a voltage of 50 kV and current of 1.00 mA, using a divergence slit of 0.3 mm and collimator of 0.3 mm. For each sample, one frame was collected using a still scan with a Pilatus 3R-100 kA detector at the distance of 154.72 mm from the sample. Raw data were evaluated using the program EVA (Bruker-AXS, Karlsruhe, Germany).

Example 1

Preparation of Deutetrabenazine Form APO-I

A mixture of Deutetrabenazine (300 mg) and 2-methyl-1-propanol (6 mL) was heated to 50° C. with stirring. To the resulting clear solution was charged quercetin dihydrate (312 mg), and the resulting suspension was stirred at 50° C. for 4 hours prior to slow cooling to room temperature. The solid was collected by filtration, washed with 2-methyl-1-propanol (2 mL), and dried in vacuo at room temperature for approximately 16 hours to afford Deutetrabenazine Form APO-I (413 mg). The PXRD diffractogram of a sample prepared by this method is shown in FIG. 1. $^1$H NMR analysis of the solid ($d_6$-DMSO)) identified a molar ratio of Deutetrabenazine:quercetin of approximately 1:1.

$^1$H-NMR of Deutetrabenazine Form APO-I ($d_6$-DMSO, 300 MHz) δ: 0.86 (t, J=6.4 Hz, 6H), 0.92 (m, 1H), 1.62 (m, 2H), 2.28 (t, J=11.8 Hz, 1H), 2.46 (m, 1H), 2.66 (m, 2H), 2.85 (dd, J=13.4, 3.0 Hz, 1H), 2.91 (m, 1H), 3.13 (m, 1H), 3.24 (dd, J=11.7, 6.0 Hz, 1H), 3.46 (d, J=11.6 Hz, 1H), 6.18 (d, J=1.9 Hz, 1H), 6.40 (d, J=2.0 Hz, 1H), 6.67 (s, 1H), 6.69 (s, 2H), 6.88 (d, J=8.5 Hz, 1H), 7.54 (dd, J=8.4, 2.0 Hz, 1H), 7.67 (d, J=2.0 Hz, 1H), 9.32 (br s, 2H), 9.62 (br s, 1H), 10.81 (br s, 1H), 12.50 (s, 1H).

Example 2

Preparation of Deutetrabenazine Form APO-II

A mixture of Deutetrabenazine (300 mg) and isopropyl alcohol (3 mL) was heated to 50° C. with stirring. To the resulting clear solution was charged water (1.5 mL) and luteolin (372 mg), and the resulting suspension was stirred at 50° C. for 4 hours prior to slow cooling to room temperature. The solid was collected by filtration, washed with a 1:1 isopropyl alcohol/water mixture (2 mL), and dried in vacuo at room temperature for approximately 16 hours to afford Deutetrabenazine Form APO-II (532 mg). The PXRD diffractogram of a sample prepared by this method is shown in FIG. 2. $^1$H NMR analysis of the solid ($d_6$-DMSO)) identified a molar ratio of Deutetrabenazine:luteolin of approximately 1:1.

$^1$H-NMR of Deutetrabenazine Form APO-II ($d_6$-DMSO, 300 MHz) δ: 0.86 (t, J=6.3 Hz, 6H), 0.93 (m, 1H), 1.62 (m, 2H), 2.28 (t, J=11.7 Hz, 1H), 2.46 (m, 2H), 2.66 (m, 2H), 2.85 (dd, J=13.5, 3.0 Hz, 1H), 2.91 (m, 1H), 3.13 (m, 1H), 3.24 (dd, J=11.6, 6.1 Hz, 1H), 3.46 (d, J=11.7 Hz, 1H), 6.19 (d, J=1.9 Hz, 1H), 6.45 (d, J=1.9 Hz, 1H), 6.67 (s, 1H), 6.69 (s, 2H), 6.89 (d, J=8.1 Hz, 1H), 7.40 (s, 1H), 7.41 (dd, J=10.7, 2.0 Hz, 1H), 12.98 (s, 1H).

Example 3

Preparation of Tetrabenazine Form APO-I

A mixture of Tetrabenazine (100 mg) and 2-methyl-1-propanol (2 mL) was heated to 50° C. with stirring. To the resulting clear solution was charged quercetin dihydrate (104 mg), and the resulting suspension was stirred at 50° C. for 3 hours prior to slow cooling to room temperature. The solid was collected by filtration, washed with 2-methyl-1-propanol (0.5 mL), and dried in vacuo at room temperature for approximately 16 hours to afford Tetrabenazine Form APO-I. The PXRD diffractogram of a sample prepared by this method is shown in FIG. 3. $^1$H NMR analysis of the solid (d$_6$-DMSO)) identified a molar ratio of Tetrabenazine:quercetin of approximately 1:1.

$^1$H-NMR of Tetrabenazine Form APO-I (d$_6$-DMSO, 300 MHz) δ: 0.86 (t, J=6.4 Hz, 6H), 0.92 (m, 1H), 1.62 (m, 2H), 2.28 (t, J=11.8 Hz, 1H), 2.46 (m, 1H), 2.66 (m, 2H), 2.85 (dd, J=13.4, 3.0 Hz, 1H), 2.91 (m, 1H), 3.13 (m, 1H), 3.24 (dd, J=11.7, 6.0 Hz, 1H), 3.46 (d, J=11.6 Hz, 1H), 3.71 (s, 6H), 6.18 (d, J=1.9 Hz, 1H), 6.40 (d, J=2.0 Hz, 1H), 6.67 (s, 1H), 6.69 (s, 2H), 6.88 (d, J=8.5 Hz, 1H), 7.54 (dd, J=8.4, 2.0 Hz, 1H), 7.67 (d, J=2.0 Hz, 1H), 9.31 (br s, 1H), 9.37 (br s, 1H), 9.60 (br s, 1H), 10.78 (br s, 1H), 12.50 (s, 1H).

Example 4

Preparation of Tetrabenazine Form APO-II

A mixture of Tetrabenazine (100 mg) and isopropyl alcohol (2 mL) was heated to 50° C. with stirring. To the resulting clear solution was charged water (5 mL) and luteolin (93 mg), and the resulting suspension was stirred at 50° C. for 3 hours prior to slow cooling to room temperature. The solid was collected by filtration, washed with a 1:1 isopropyl alcohol/water mixture (0.5 mL), and dried in vacuo at room temperature for approximately 16 hours to afford Tetrabenazine Form APO-II. The PXRD diffractogram of a sample prepared by this method is shown in FIG. 4. $^1$H NMR analysis of the solid (d$_6$-DMSO)) identified a molar ratio of Tetrabenazine:luteolin of approximately 1:1.

$^1$H-NMR of Tetrabenazine Form APO-II (d$_6$-DMSO, 300 MHz) δ: 0.86 (t, J=6.3 Hz, 6H), 0.93 (m, 1H), 1.62 (m, 2H), 2.28 (t, J=11.7 Hz, 1H), 2.46 (m, 2H), 2.66 (m, 2H), 2.85 (dd, J=13.5, 3.0 Hz, 1H), 2.91 (m, 1H), 3.13 (m, 1H), 3.24 (dd, J=11.6, 6.1 Hz, 1H), 3.46 (d, J=11.7 Hz, 1H), 3.71 (s, 6H), 6.19 (d, J=1.9 Hz, 1H), 6.45 (d, J=1.9 Hz, 1H), 6.67 (s, 1H), 6.69 (s, 2H), 6.89 (d, J=8.1 Hz, 1H), 7.40 (s, 1H), 7.41 (dd, J=10.7, 2.0 Hz, 1H), 12.98 (s, 1H).

What is claimed is:

1. A crystalline form of Deutetrabenazine and quercetin characterized by a PXRD diffractogram comprising peaks, expressed in degrees 2θ (±0.2°), at 6.2°, 9.3° and 14.1°.

2. The crystalline form of claim 1, wherein the molar ratio of Deutetrabenazine to quercetin is 1:1.

3. The crystalline form of claim 1, further comprising at least three peaks, expressed in degrees 2θ (±0.2°), selected from the group consisting of: 6.9°, 10.3°, 11.1°, 12.4°, 15.7° and 18.6°.

4. The crystalline form of claim 1, further comprising peaks, expressed in degrees 2θ (±0.2°), at 6.9°, 10.3°, 11.1°, 12.4°, 15.7° and 18.6°.

5. The crystalline form of claim 1 providing a PXRD diffractogram substantially the same in appearance as the PXRD diffractogram provided in FIG. 1.

6. A crystalline form of Deutetrabenazine and luteolin, characterized by a PXRD diffractogram comprising peaks, expressed in degrees 2θ (±0.2°) at 6.2°, 9.3° and 14.2°.

7. The crystalline form of claim 6, wherein the molar ratio of Deutetrabenazine to luteolin is 1:1.

8. The crystalline form of claim 6, further comprising at least three peaks, expressed in degrees 2θ (±0.2°), selected from the group consisting of: 6.9°, 10.3°, 11.1°, 12.4°, 15.7° and 18.6°.

9. The crystalline form of claim 6, further comprising peaks, expressed in degrees 2θ (±0.2°), at 6.9°, 10.3°, 11.1°, 12.4°, 15.7° and 18.6°.

10. The crystalline form of claim 6 providing a PXRD diffractogram substantially the same in appearance as the PXRD diffractogram provided in FIG. 2.

11. A pharmaceutical composition comprising a crystalline form of Deutetrabenazine and quercetin or luteolin and one or more pharmaceutically acceptable excipients, wherein:
the crystalline form of Deutetrabenazine and quercetin is characterized by a PXRD diffractogram comprising peaks, expressed in degrees 2θ (±0.2°), at 6.2°, 9.3° and 14.1°; and
the crystalline form of Deutetrabenazine and luteolin is characterized by a PXRD diffractogram comprising peaks, expressed in degrees 2θ (±0.2°), at 6.2°, 9.3° and 14.2°.

12. The pharmaceutical composition of claim 11 comprising a crystalline form of Deutetrabenazine and quercetin characterized by a PXRD diffractogram comprising peaks, expressed in degrees 2θ (±0.2°), at 6.2°, 9.3° and 14.1°.

13. The pharmaceutical composition of claim 11 comprising a crystalline form of Deutetrabenazine and luteolin characterized by a PXRD diffractogram comprising peaks, expressed in degrees 2θ (±0.2°), at 6.2°, 9.3° and 14.2°.

14. The pharmaceutical composition of claim 11, wherein the pharmaceutical composition is a tablet.

15. The pharmaceutical composition of claim 12, wherein the pharmaceutical composition is a tablet.

16. The pharmaceutical composition of claim 13, wherein the pharmaceutical composition is a tablet.

* * * * *

UNITED STATES PATENT AND TRADEMARK OFFICE
CERTIFICATE OF CORRECTION

PATENT NO. : 10,632,107 B2
APPLICATION NO. : 16/410248
DATED : April 28, 2020
INVENTOR(S) : Fabio E. S. Souza et al.

Page 1 of 1

It is certified that error appears in the above-identified patent and that said Letters Patent is hereby corrected as shown below:

In the Claims

Column 16, Line 9, Claim 6, after "(±0.2°)" insert -- , --

Column 16, Line 33, Claim 11, delete "14.2° ." and insert -- 14.2°. --

Signed and Sealed this
Fourth Day of August, 2020

Andrei Iancu
*Director of the United States Patent and Trademark Office*